(12) United States Patent
Green et al.

(10) Patent No.: US 9,968,762 B2
(45) Date of Patent: May 15, 2018

(54) WIRE GUIDE WITH MULTIPLE TIPS (75) Inventors: Sara M. Green, Bloomington, IN (US); Kurt J. Tekulve, Ellettsville, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1419 days.

(21) Appl. No.: 13/569,758

(22) Filed: Aug. 8, 2012

(65) Prior Publication Data
US 2014/0046302 A1    Feb. 13, 2014

(51) Int. Cl.
*A61B 5/00* (2006.01)
*A61M 25/00* (2006.01)
*A61M 25/09* (2006.01)

(52) U.S. Cl.
CPC ... *A61M 25/09* (2013.01); *A61M 2025/09083* (2013.01); *A61M 2025/09175* (2013.01)

(58) Field of Classification Search
CPC .............. A61M 25/09; A61M 25/0108; A61B 2017/22038
USPC ........................................ 600/585; 604/528
See application file for complete search history.

(56) References Cited

U.S. PATENT DOCUMENTS

| | | | |
|---|---|---|---|
| 4,827,941 A | 5/1989 | Taylor et al. | |
| 4,875,489 A | 10/1989 | Messner et al. | |
| 4,907,332 A | 3/1990 | Christain et al. | |
| 4,917,103 A | 4/1990 | Gambale et al. | |
| 4,922,923 A | 5/1990 | Gambale et al. | |
| 4,922,924 A * | 5/1990 | Gambale | A61M 25/09 600/434 |
| 4,966,163 A | 10/1990 | Kraus et al. | |
| 5,031,636 A | 7/1991 | Gambale et al. | |
| 5,035,686 A | 7/1991 | Crittenden et al. | |
| 5,060,660 A | 10/1991 | Gambale et al. | |
| 5,109,867 A * | 5/1992 | Twyford, Jr. | A61M 25/0905 403/223 |
| 5,113,872 A | 5/1992 | Jahrmarkt et al. | |
| 5,117,838 A | 6/1992 | Palmer et al. | |
| 5,133,364 A | 6/1992 | Palermo et al. | |
| 5,139,032 A | 8/1992 | Jahrmarkt et al. | |
| 5,144,959 A * | 9/1992 | Gambale | A61M 25/09 600/434 |
| 5,163,903 A | 11/1992 | Crittenden et al. | |
| 5,174,302 A * | 12/1992 | Palmer | A61M 25/09 600/434 |
| 5,188,621 A | 2/1993 | Samson | |
| 5,191,888 A | 3/1993 | Palmer et al. | |
| 5,195,535 A | 3/1993 | Shank | |
| 5,195,978 A | 3/1993 | Schiffer | |
| 5,234,002 A | 8/1993 | Chan | |
| 5,234,407 A | 8/1993 | Teirstein et al. | |

(Continued)

OTHER PUBLICATIONS

US 5,197,486, 03/1993, Frassica (withdrawn)

(Continued)

*Primary Examiner* — May Abouelela
(74) *Attorney, Agent, or Firm* — Brinks Gilson & Lione (57) ABSTRACT

A medical wire guide may include a mandril having a distal tip, a first coil coupled with the distal tip of the mandril, and a second coil configured to releasably engage with the mandril or the first coil. The second coil comprises a distal tip and defines an inner cavity dimensioned to contain a distal tip of the first coil when the second coil is engaged with the mandril or the first coil.

15 Claims, 6 Drawing Sheets

(56) References Cited

U.S. PATENT DOCUMENTS

| | | | |
|---|---|---|---|
| 5,246,009 A | 9/1993 | Adams | |
| 5,247,942 A | 9/1993 | Prather et al. | |
| 5,255,690 A | 10/1993 | Keith et al. | |
| RE34,466 E | 12/1993 | Taylor et al. | |
| 5,267,573 A | 12/1993 | Evans et al. | |
| 5,269,759 A | 12/1993 | Hernandez et al. | |
| 5,271,415 A | 12/1993 | Foerster et al. | |
| 5,275,173 A | 1/1994 | Samson et al. | |
| 5,281,203 A | 1/1994 | Ressemann | |
| 5,282,478 A | 2/1994 | Fleischhaker, Jr. et al. | |
| 5,345,945 A * | 9/1994 | Hodgson | A61M 25/09033 600/433 |
| 5,365,944 A * | 11/1994 | Gambale | A61M 25/0905 600/585 |
| 5,377,690 A * | 1/1995 | Berthiaume | A61M 25/09 600/585 |
| 5,421,348 A * | 6/1995 | Larnard | A61M 25/0905 600/434 |
| 5,441,055 A | 8/1995 | Ales et al. | |
| 5,788,653 A * | 8/1998 | Lorenzo | A61M 25/0905 600/585 |
| 5,954,672 A * | 9/1999 | Schwager | A61B 5/6851 600/585 |
| 6,039,700 A | 3/2000 | Sauter | |
| 6,099,485 A | 8/2000 | Patterson | |
| 6,491,646 B1 * | 12/2002 | Blackledge | A61M 25/0905 600/585 |
| 6,527,732 B1 * | 3/2003 | Strauss | A61M 25/09 600/585 |
| 6,911,016 B2 | 6/2005 | Balzum et al. | |
| 7,637,875 B2 * | 12/2009 | Itou | A61M 25/09 600/434 |
| 8,425,537 B2 * | 4/2013 | Mitelberg | A61B 17/12022 606/139 |
| 2008/0051676 A1 | 2/2008 | Melsheimer et al. | |
| 2012/0220896 A1 * | 8/2012 | Matsuo | A61M 25/09 600/585 |
| 2014/0024968 A1 * | 1/2014 | Echarri | A61M 25/09 600/585 |

OTHER PUBLICATIONS

Peripheral Vascular Product Catalog 2012; Covidien, Plymouth, Minnesota; Copyright 2011; 36 pages.

Cook Medical Wire Guides Catalog; Cook Medical, Copyright 2010; 28 pages.

Tru Tech Revolution Perimetric™ Grinding System; Tru Tech Systems, Inc.; Screenshot downloaded from http://www.trutechsystems.com/ on Sep. 18, 2012; 1 page.

Kine-Coil Precision CNC Coiling Technology ; Kinefac Corporation; webpage downloaded from http://www.microcoiler.com/ on Sep. 18, 2012; 1 page.

EV3 Receives FDA Clearance for SpideRX™ Embolic Protection Device for Saphenous Vein Graft Angioplasty; Jun. 26, 2006; PRNewswire United Business Wire; http://www.prnewswire.com/news-releases/ev3-receives-fda-clearance-for-spiderxtm-embolic-protection-device-for-saphenous-vein-graft-angioplasty-56959097.html; 2 pages.

* cited by examiner

WIRE GUIDE WITH MULTIPLE TIPS

TECHNICAL FIELD

This application relates to medical devices and, more particularly, to a wire guide with a plurality of usable tips.

BACKGROUND

Wire guides are commonly used to introduce a wide variety of medical devices into a patient's vascular system or other bodily lumen. For example, wire guides may be used in angioplasty procedures, diagnostic and interventional procedures, percutaneous access procedures, or radiological and neuroradiological procedures in general. A traditional wire guide may include an elongated core element and a flexible helical coil at a distal end portion of the core element. The wire guide may also include a handle at the proximal end of the core element to steer the wire guide as it is being advanced through a patient's vascular system or other bodily lumen.

Wire guides may encounter various challenges as they are moved through a patient's vascular system or other bodily lumen. As one example, in a pedal access procedure the wire guide is inserted from the foot (pedal) so that the wire guide can traverse up into the leg below the target site. In such a procedure, assistance may be needed to direct the distal tip of the wire guide into a branch of the limb's vascular system. For example, the wire guide may experience a 90 degree or greater turn from the main vessel into the branching targeted vessel. Therefore, a physician may insert a snare into the patient from a second access location above the target site. The physician may use the snare to grab the wire guide at the tip and direct it into the branching vessel. Although the snare may help guide the tip of the wire guide, this contact between the snare and the wire guide tip may permanently damage the tip.

A wire guide may also be damaged in other procedures. For example, the patient's vascular system or other bodily lumen may contain occlusions that impede the wire guide along its path. The physician may attempt to break apart the occlusion by pushing the wire guide through the occlusion, but this contact between the distal tip of the wire guide and the occlusion may damage the distal tip.

When the distal tip of the wire guide is damaged, further use of the wire guide may be difficult for the physician or dangerous to the patient. Thus, a need exists for an improved wire guide.

BRIEF SUMMARY

In one implementation, a medical wire guide is provided that includes a mandril having a distal tip, a first coil coupled with the distal tip of the mandril, and a second coil configured to releasably engage with the mandril or the first coil. The second coil comprises a distal tip and defines an inner cavity dimensioned to contain a distal tip of the first coil when the second coil is engaged with the mandril or the first coil.

In another implementation, a medical wire guide is provided that includes a mandril having a distal tip, a first coil coupled with the distal tip of the mandril, and a second coil. The first coil has an interlocking portion and a distal end portion. The distal end portion of the first coil tapers in from a dimension of the interlocking portion of the first coil. The second coil has an interlocking portion, a distal end portion, and an inner cavity between the interlocking portion and the distal end portion. The interlocking portion of the first coil is dimensioned to releasably engage with the interlocking portion of the second coil. The distal end portion of the first coil is contained within the inner cavity of the second coil when the interlocking portion of the second coil is engaged with the interlocking portion of the first coil.

In yet another implementation, a medical wire guide is provided that includes a mandril having a body portion and a distal tip, a first coil coupled with the distal tip of the mandril, a cannula having a proximal end and a distal end, and a second coil having a proximal end and a distal end. The proximal end of the cannula is configured to releasably engage with the body portion of the mandril, and the first coil is contained within the inner cavity of the second coil when the cannula is engaged with the body portion of the mandril.

BRIEF DESCRIPTION OF THE DRAWINGS

The components in the figures are not necessarily to scale. Moreover, in the figures, like referenced numerals designate corresponding parts throughout the different views.

DETAILED DESCRIPTION

This detailed description describes a medical wire guide that possesses a plurality of usable tips. For example, a first one of the wire guide tips may be used and then removed, revealing a fresh tip that resides beneath the first tip on the same end of the wire guide. A wire guide with multiple usable tips may be especially beneficial for medical procedures that require different tip properties at different stages of the procedure or for medical procedures that commonly result in damage to the leading tip of the wire guide. For example, a wire guide with multiple tips would allow a physician to remove a damaged wire guide tip and then continue to use the same wire guide with the newly revealed second tip to complete the procedure. Having multiple usable tips in a wire guide could save the time and materials that would otherwise be wasted by removing the damaged wire guide and inserting a new wire guide to complete the procedure after the first wire guide was damaged. These savings are especially helpful given the rise of health care costs.

The wire guide assemblies described herein are formed from a plurality of components, including mandrils, coils, safety wires, and cannulas, which will each be described below in connection with FIGS. 1-22. As used herein, the term "proximal" refers to a portion of the wire guide (or a portion of any device component) closer than another portion to a physician when the wire guide is inserted into a patient, and the term "distal" refers to a portion of the wire guide (or a portion of any device component) closer than another portion to the end of the wire guide that is inserted into the patient's body.

Figure 1:
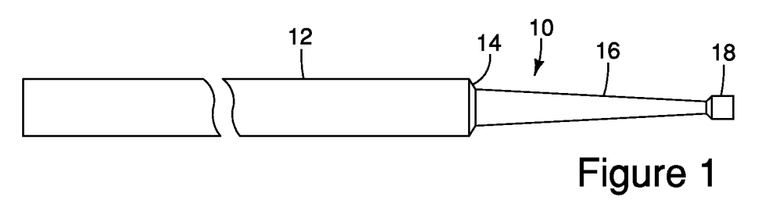
FIG. 1 illustrates a mandril for a wire guide.

FIG. 1 illustrates a mandril 10 for a wire guide. The mandril 10 of FIG. 1 includes a body portion 12, a shoulder portion 14, a tapered distal portion 16, and a distal tip 18. The mandril 10 may comprise a core wire or solid shaft with a distal end and a proximal end. The distal tip 18 may be disposed at the distal end of the mandril 10. A handle (not shown) may be disposed at the proximal end of the mandril 10. The handle may be used to pull the mandril 10 in a proximal direction. Alternatively or additionally, the handle may be used to push the mandril 10 in a distal direction or twist the mandril 10. Such manipulations may steer the wire guide along its path through the vascular system or other lumen. The handle may be formed to have a low profile so that a medical device (e.g., a catheter) may pass over the handle and continue to pass over the remainder of the wire guide unimpeded.

The mandril 10 may be formed of a suitable metallic material such as medical grade stainless steel, a stainless steel alloy, a super-elastic material including a nickel-titanium alloy (e.g., Nitinol), a liner-elastic material, or combinations of these materials. Alternatively, other suitable mandril materials may be used. The mandril 10 may include a radiopaque material, such as platinum or gold. Inclusion of a radiopaque material may increase the visibility of the wire guide within the body of a patient. In some implementations, a radiopaque material may be included in other portions of the wire guide, such as in the various coils, safety wires, and cannulas.

It will be appreciated that the mandril 10 may take one of many different shapes. In some implementations, the mandril 10 has a circular cross-sectional shape. In other implementations, the mandril 10 has a rectangular cross-sectional shape. In yet other implementations, the cross-section of the mandril 10 assumes different shapes along the length of the mandril 10. The mandril 10 may have a cross-sectional area that remains substantially constant along its length. Alternatively, the mandril 10 may have a cross-sectional area that varies along its length. In one implementation, the mandril 10 has a cross-sectional area that diminishes gradually or stepwise at increasing distances from the proximal end of the wire guide such that the mandril 10 tapers to a smaller diameter toward its distal end. For example, as shown in FIG. 1, the mandril 10 may include the tapered distal portion 16 of a reduced diameter. The tapered distal portion 16 may increase the flexibility of the distal end of the wire guide.

The shoulder portion 14 of the mandril 10 may be ground into the beginning of the taper to provide a supporting surface for abutting a coil. The shoulder portion 14 may also provide a soldering surface for connecting a coil with the mandril 10. In one implementation, the shoulder portion 14 may be larger than the diameter of the coil abutting the shoulder portion 14 so that the coil cannot pass over the shoulder portion 14. The distal tip 18 of the mandril 10 may include a barrel at the end of the taper. The barrel of the distal tip 18 may provide support and an increased surface area for binding with a coil.

Figure 2:
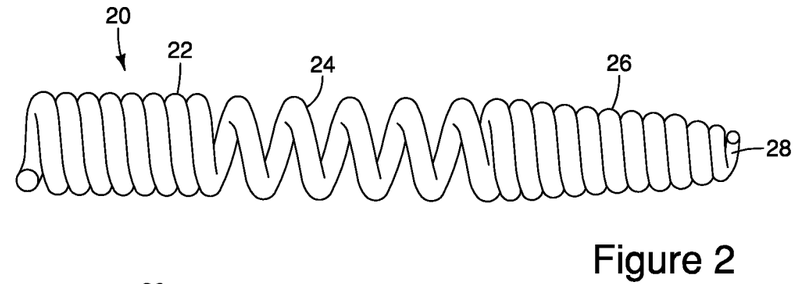
FIGS. 2 and 3 illustrate coils for a wire guide.

FIG. 2 illustrates a coil 20 for one implementation of a wire guide assembly. The coil 20 may be a helical shaped wound coil formed by winding a wire into a plurality of rings (e.g., wire turns). The coil 20 may be wound by a coiling machine that presses the wire against a wedge to make the wire curve into a coil shape. The coiling machine can control the pitch and diameter of the coil according to the operator's preferences. The wire used to form the coil 20 may be made from a suitable metallic material such as platinum, palladium, medical grade stainless steel, a stainless steel alloy, a super-elastic material including a nickel-titanium alloy (e.g., Nitinol), a liner-elastic material, or combinations of these materials. Alternatively, other suitable coil winding materials may be used for the coil 20.

The coil 20 includes a proximal end portion 22, an interlocking portion 24, and a distal end portion 26. The interlocking portion 24 may have a different winding pitch than the proximal end portion 22 and the distal end portion 26. For example, as shown in FIG. 2, a plurality of coil rings in the middle of the coil 20 may have a larger pitch/width than the coil rings of the proximal and distal ends. In one implementation, three to five coil rings in the interlocking portion 24 of the coil 20 have a larger pitch/width than the majority of the coil 20. In other implementations, more or fewer coil rings may be included as part of the interlocking portion 24.

In one implementation, the proximal end portion 22 may represent 40% or more of the total length of the coil 20, the interlocking portion 24 may represent 10% of the total length of the coil 20, and the distal end portion 26 may represent 40% or less of the total length of the coil 20. Alternatively, other proportions of the length of the coil may be devoted to the respective portions.

The entire length of the proximal end portion 22 and the interlocking portion 24 of the coil 20 may have about an equal diameter (e.g., within either a 5%, 10%, or 20% variation in diameter). Alternatively, some portions of the proximal end portion 22 or the interlocking portion 24 may taper to a narrower diameter or extend to a wider diameter. The distal end portion 26 of the coil 20 tapers in from a dimension (e.g., diameter) of the interlocking portion 24 such that a distal-most segment 28 of the distal end portion 26 is smaller in diameter than the diameter of the interlocking portion 24 and may be smaller in diameter than other sections of the distal end portion 26.

Figure 3:
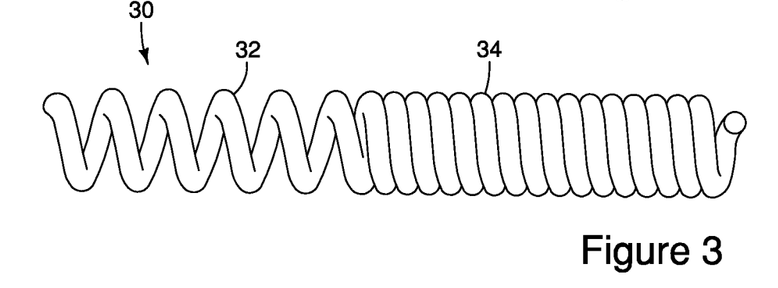

FIG. 3 illustrates a coil 30 that is connectable with the coil 20 of FIG. 2 in a wire guide assembly. The coil 30 may be a helical shaped wound coil formed by winding a wire into a plurality of rings (e.g., wire turns). The wire used to form the coil 30 may be made from a suitable metallic material such as platinum, palladium, medical grade stainless steel, a stainless steel alloy, a super-elastic material including a nickel-titanium alloy (e.g., Nitinol), a liner-elastic material, or combinations of these materials. Alternatively, other suitable coil winding materials may be used for the coil 30.

The coil 30 may include an interlocking portion 32 and a distal end portion 34. The interlocking portion 32 may have a different winding pitch than the distal end portion 34. For example, as shown in FIG. 3, a plurality of coil rings at the proximal end of the coil 30 may have a larger pitch/width than the coil rings of the distal end portion 34. In one implementation, three to five coil rings at the proximal end of the coil 30 have a larger pitch/width than the majority of the coil 30. In other implementations, more or fewer coil rings may be included as part of the interlocking portion 32. The entire length of the coil 30 may have about an equal diameter (e.g., within either a 5%, 10%, or 20% variation in diameter). Alternatively, some portions of the coil 30 may taper to a narrower diameter or extend to a wider diameter.

Figure 4:
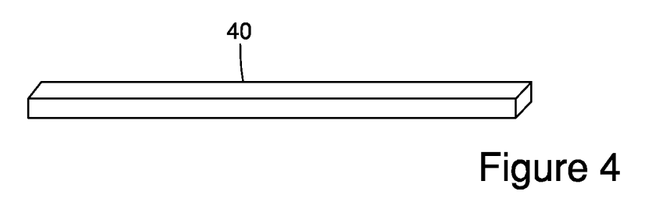
FIG. 4 illustrates a safety wire for a wire guide.
Figure 5:
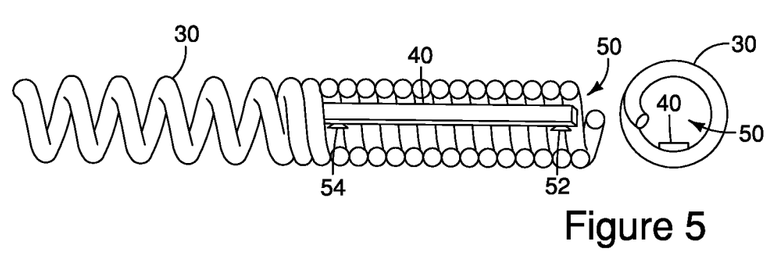
FIG. 5 illustrates the safety wire of FIG. 4 coupled with the coil of FIG. 3.

FIG. 4 illustrates a safety wire 40 for a wire guide. Each of the coils used in the wire guides described herein may be connected with a safety wire 40 to prevent the coil from being stretched or completely separated from the mandril at either end. FIG. 5 illustrates the safety wire 40 of FIG. 4 coupled with the coil 30 of FIG. 3. The left side of FIG. 5 shows a cut-away side view of the coil 30 and the safety wire 40, while the right side of FIG. 5 shows an end view looking down an inner cavity 50 of the coil 30. As shown in FIG. 5, the safety wire 40 may connect a distal end portion of the coil 30 to a proximal end portion of the coil 30. The safety wire 40 may pass through the inner cavity 50 of the coil 30. The connection between the safety wire 40 and the coil 30 may be performed by soldered connections 52 and 54. The safety wire 40 may run at least a portion of the length of the interior cavity 50 of the coil 30 to ensure longitudinal integrity of at least a portion of the coil 30 and limit some movement (e.g., stretch) of the distal end of the coil 30 relative to the proximal end of the coil 30. The connection of the safety wire 40 to a coil may occur separately in the material preparation stage, before assembly of the final product. Alternatively, the safety wire 40 may be connected to the coil during the assembly of the final product.

Figure 6:
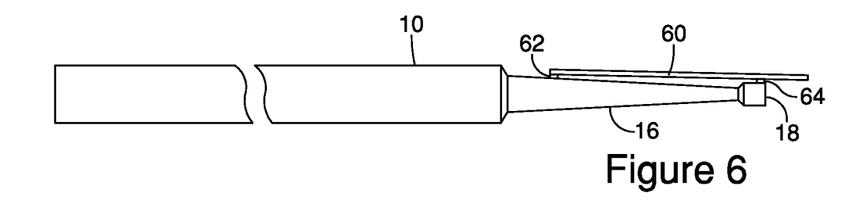
FIGS. 6-10 illustrate a first wire guide assembly using the components of FIGS. 1-5.
Figure 7:
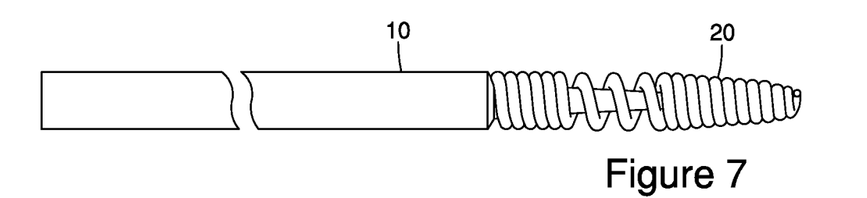

FIGS. 6-10 illustrate a first wire guide assembly using the components of FIGS. 1-5. As shown in FIG. 6, a safety wire 60 may be connected to the mandril 10. For example, soldered connections 62 and 64 may bond the safety wire 60 to the mandril 10, such as at the barrel and taper of the mandril 10. The safety wire 60 used in FIG. 6 may be similar in construction as the safety wire 40 described above in connection with FIGS. 4 and 5. In one implementation, the safety wire 60 is long enough to span the length of the wider pitch portion of the coil (e.g., the interlocking portion of the coil 20 shown in FIG. 7) that will be connected over the safety wire 60. As shown in FIG. 7, the coil 20 is added over the safety wire 60 and the tapered distal end portion of the mandril 10 of FIG. 6. The coil 20 may be bonded with the safety wire 60 and/or the mandril 10 via one or more soldered connections.

Figure 8:
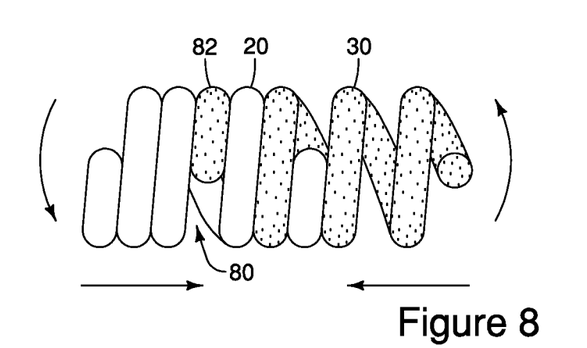

FIG. 8 illustrates a connection between the coil 30 and the coil 20. For example, the coil 30 is added to the assembly illustrated in FIG. 7 by slipping the coil 30 over the coil 20 and aligning the respective interlocking portions (e.g., the wider pitch portions). The coil 30 is twisted relative to the coil 20 so that the interlocking portions intertwine together and form the appearance of one solid coil. The interlocking portion of the coil 20 has a wider pitch than other areas of the coil 20 to define a space 80 between adjacent rings of the coil 20. The space is dimensioned to fit a corresponding ring 82 of the coil 30 when the interlocking portion of the coil 30 is engaged with the interlocking portion of the coil 20.

In one implementation, the coil 20 is soldered to the mandril 10, while the coil 30 is free from a direct connection with the mandril 10. For example, the coil 30 may be coupled with the mandril 10 by an indirect connection through a threaded engagement with the coil 20. The threaded engagement may be disconnected by twisting the coil 30 relative to the coil 20 in the opposite direction than used to connect the coil 30 with the coil 20.

Figure 9:
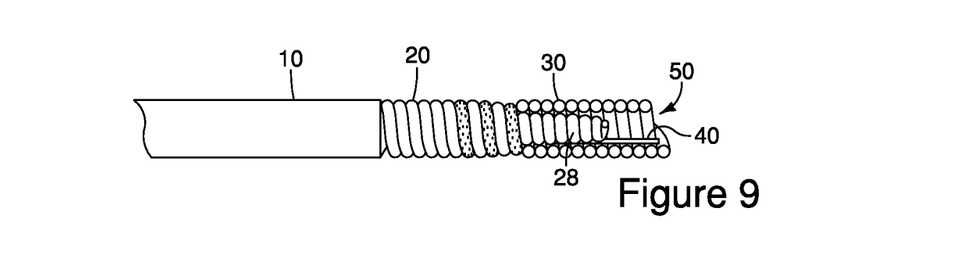

As shown in FIG. 9, the tip of one coil may be covered by the tip of another coil. For example, the distal tip 28 of the coil 20 may be contained within the inner cavity 50 of the coil 30 when the coil 30 is engaged with the coil 20. Thus, at least a portion of the distal tip 28 of the coil 20 resides beneath the coil 30 when the two coils are engaged. The inner coil 20 may thus be protected from at least some damage while the outer coil 30 is connected with the inner coil 20.

Figure 10:
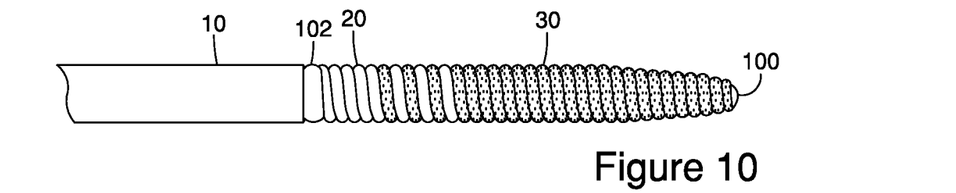

Each of the distal tips of the coils may be formed to promote atraumatic vessel navigation, such as by forming a rounded distal surface. The distal-most portion of the distal tip 28 of the coil 20 may be welded or soldered to form an atraumatic distal tip usable after the outer coil 30 is removed from the wire guide. As shown in FIG. 10, a distal-most tip 100 of the coil 30 may also be welded or soldered to form another atraumatic distal tip usable before the outer coil 30 is removed from the wire guide. Additionally, the wire guide may include a solder joint 102 to connect the coil 20 with the mandril 10. FIG. 10 illustrates the wire guide in final assembled form with multiple usable distal tips on the same end of the wire guide, one tip from the outer coil 30 and one tip from the inner coil 20.

During a medical procedure, a physician may use the distal end of the coil 30 as the leading distal tip of the wire guide for a first stage of the procedure. At some point in the procedure, the physician may want to remove the coil 30 and expose the underlying coil 20 to act as the leading distal tip of the wire guide for another stage of the procedure. As one example, the physician may want to remove the coil 30 because it has been damaged. As another example, the physician may want to remove the coil 30 because the coil 20 has certain properties, such as an increased flexibility, that are better suited for the next stage of the procedure.

A physician may remove the coil 30 from the wire guide by pushing the distal end of the wire guide out of a second access location of the patient that is different than the first access location that was used to begin feeding the wire guide into the patient. The distal end of the wire guide may be exposed while other portions of the wire guide are still within a vascular passage or other bodily lumen of the patient. The coil 30 may be removed by locating an area distal to the intertwined coils and twisting the coil 30 relative to the coil 20 to disengage the threaded connection between the two coils. The interlocking portions may be visually marked in some way to enhance the ability of the physician to locate the area of connection between the coils. The threaded connection provides a simple removal process that may not require tools. Additionally, the threaded connection is unlikely to unscrew with torsion while in the patient. After the coil 30 has been removed to expose the distal tip of the coil 20, then the new distal tip of the wire guide may be retracted back into the patient through the second access location to continue the medical procedure with the distal tip of the coil 20 now serving as the distal-most portion of the wire guide.

Having two different usable distal tips available on one end of the wire guide allows customization of the two tips for different stages of the procedure. As a first example, the first coil 20 may be formed from a different material than the coil 30. The different properties of the materials may allow the coil 30 to be formed from a relatively stiff material for clearing occlusions, while the coil 20 may be formed from a relatively flexible material for traversing delicate passageways after the occlusions have been cleared. As a second example, the distal end portion of the coil 30 may be wound with a different pitch than the distal end portion of the coil 20. The different winding pitches may allow one coil to be stiffer or more flexible than the other. As a third example, the coil 30 may be wound from a wire with a different diameter than a wire used for the coil 20. The different wire diameters may allow one coil to be stiffer or more flexible than the other. As a fourth example, the diameter of the coil 20 may be smaller than the diameter of the coil 30. This difference in size may allow the wire guide to gain access to smaller passageways when led by the coil 20 after the larger coil 30 is removed from the wire guide. As a fifth example, one of the coils may have a curved shape. For example, the outer coil 30 may be separately curved so that the curved portion extends beyond the length of the inner coil 20. This difference in coil shape allows for a wire guide with both a curved distal tip option and a straight distal tip option. Alternatively, both coils 20 and 30 may be attached together while straight and then curved together at the same time. This implementation provides a wire guide with multiple curved usable tips. One or more of the coils may be curved by stretching the coil in a manner that provides space between adjacent coil rings to define the curve radius.

Additionally, the coils may be different from each other in multiple ways. For example, the distal tip of the coil 30 may be made of stainless steel with a very tight pitch and/or larger wire to create great stiffness for pushing through blockages, and the distal tip of the coil 20 that is contained beneath the coil 30 may be made of a softer material with a wider pitch and/or a smaller wire diameter for use further into the body as vessels become smaller or more fragile. Thus, the combinations of materials, coil pitches, coil diameters, and wire sizes result in a multi-purpose wire guide that may be customized to the unique set of requirements of an individual procedure.

Although the differences in properties between the coils 20 and 30 may provide a benefit in some procedures and implementations, in other procedures and implementations there may be a benefit to having multiple available distal tips with the same or similar properties. For example, the coil 20 may have many of the same properties as the coil 30, and thus serves as a redundant distal tip in case the coil 30 is damaged during use. In this situation, the coil 20 is available for use as the distal tip to continue the procedure after the damaged coil 30 has been removed. Having multiple redundant distal tips on the wire guide may provide a solution to replacing damaged wire guide tips by saving procedural time, hospital materials, and healthcare and procedural costs. It saves time and reduces the possibility of contamination by providing a ready, fresh wire guide tip without requiring the physician to fully remove the whole damaged wire guide and insert an entirely new wire guide to complete the procedure. For example, contamination may become an increasing concern when the wire in use has a length longer than 80 cm, which may require many personnel to assist in handling. By not requiring the complete removal of the wire guide in some implementations to get a new usable distal tip for the wire guide, the risk of contamination, lost time, and lost costs is reduced.

FIGS. 1-10, as discussed above, illustrate a first implementation of a wire guide with multiple tips on the distal end of the wire guide. FIGS. 11-22 illustrate a second implementation of a wire guide with multiple tips on the distal end of the wire guide. The implementation of FIGS. 11-22 includes many of the same features and benefits as the implementation of FIGS. 1-10. For example, the implementation of FIGS. 11-22 allows the customization of the properties of multiple distal tips (e.g., by selection of different materials, coil pitches, coil sizes, or the like) and allows for the removal of a damaged distal tip to expose an underlying distal tip usable to complete the procedure, as discussed above in connection with the implementation of FIGS. 1-10. Therefore, the properties and features discussed above in connection with the implementation of FIGS. 1-10 are equally applicable to the corresponding components of the implementation of FIGS. 11-22 unless otherwise stated.

Figure 11:
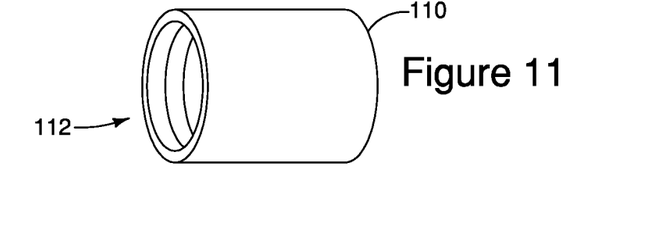
FIGS. 11-13 illustrate a cannula for a wire guide.
Figure 12:
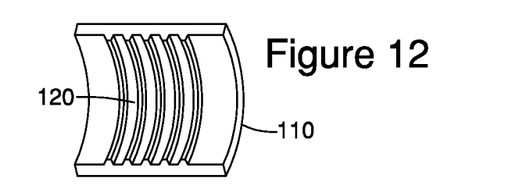
Figure 13:
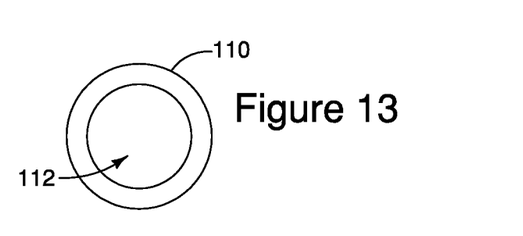

FIGS. 11-13 illustrate a cannula 110 for the second wire guide implementation. Specifically, FIG. 11 illustrates an isometric view of the cannula 110, FIG. 12 illustrates a partial cross-section view of the cannula 110, and FIG. 13 illustrates an end view of the cannula 110. The cannula 110 may be formed of a suitable metallic material such as medical grade stainless steel, a stainless steel alloy, a super-elastic material including a nickel-titanium alloy (e.g., Nitinol), a liner-elastic material, or combinations of these materials. Alternatively, other suitable mandril materials may be used. The cannula 110 acts as a coil base to connect a coil with a mandril. The cannula 110 includes a hollow cylindrical passageway 112. The inner surface of the cannula 110 (e.g., the inner surface of the hollow cylindrical passageway 112) includes threads 120. The threads may be used to connect the cannula 110 with corresponding threads of a mandril. Other connection devices, such as latches or tabs, may be used in place of the threads to connect the cannula 110 with the mandril. In one implementation, the cannula 110 is the about the same diameter (e.g., within either a 5%, 10%, or 20% variation in diameter) as the coil that will be connected with the cannula 110.

Figure 14:
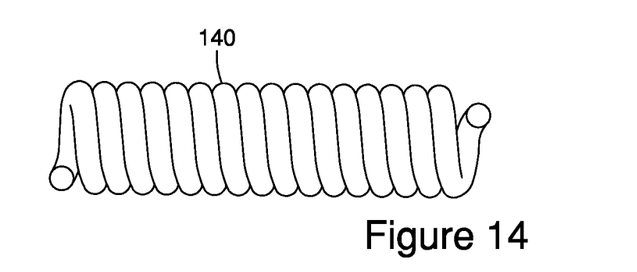
FIGS. 14 and 15 illustrate coils for a wire guide.
Figure 15:
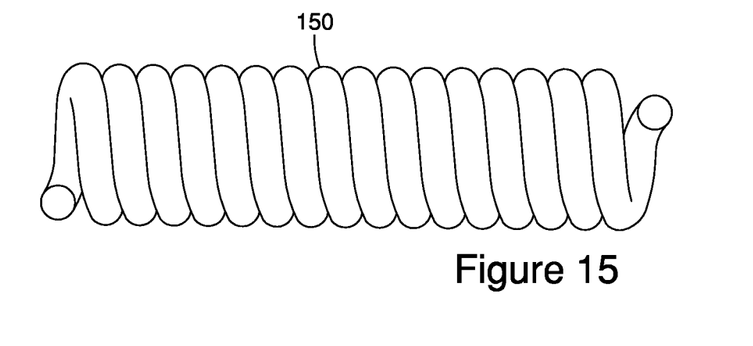

FIGS. 14 and 15 illustrate coils 140 and 150 for use with the second wire guide implementation. The coils 140 and 150 may be uniform diameter coils. For example, the entire length of each of the coils 140 and 150 may have about an equal diameter (e.g., within either a 5%, 10%, or 20% variation in diameter), although the uniform diameter of the coil 140 may be different than the uniform diameter of the coil 150. Alternatively, some portions of the coils 140 and 150 may taper to a narrower diameter or extend to a wider diameter. In one implementation, the coil 140 is smaller than the coil 150. For example, the diameter of the coil 140 may be smaller than the diameter 150 so that the coil 140 is able to fit within an inner cavity of the coil 150.

The coils 140 and 150 may be helical shaped wound coils formed by winding a wire to form a plurality of rings (e.g., wire turns). The coils may be wound by a coiling machine that presses the wire against a wedge to curve the wire into a coil shape. The coiling machine can control the pitch and diameter of the coil according to the operator's preferences. The wire used to form the coils 140 and 150 may be made from a suitable metallic material such as platinum, palladium, medical grade stainless steel, a stainless steel alloy, a super-elastic material including a nickel-titanium alloy (e.g., Nitinol), a liner-elastic material, or combinations of these materials. Alternatively, other suitable coil winding materials may be used for the coils 140 and 150.

One or both of the coils 140 and 150 may include a safety wire (e.g., similar to the safety wire 40 shown in FIGS. 4 and 5) to prevent the coil from being stretched or completely separated from the mandril at either end. The safety wire may connect a distal end portion of the coil to a proximal end portion of the coil within an inner cavity of the coil. The connection between the safety wire and the coil may be performed by soldered connections. The safety wire may run at least a portion of the length of the interior cavity of the coil to ensure longitudinal integrity of the coil and limit some movement (e.g., stretch) of the distal end of the coil relative to the proximal end of the coil. The connection of the safety wire to a coil may occur separately in the material preparation stage, before assembly of the final product. Alternatively, the safety wire may be connected to the coil during the assembly of the final product.

Figure 16A:
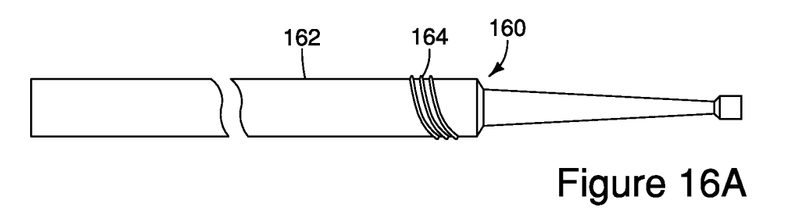
FIGS. 16A and 16B illustrate a mandril for a wire guide.
Figure 16B:
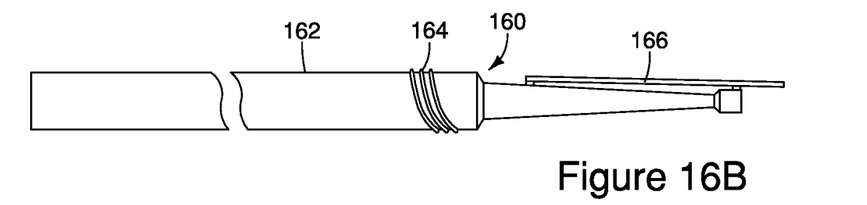

FIG. 16 illustrates a mandril 160 for a wire guide. FIG. 16A shows the mandril 160 without a safety wire, and FIG. 16B shows a safety wire 166 coupled with the mandril 160. The mandril 160 of FIG. 16 is similar to the mandril 10 of FIG. 1 and shares many of the properties of the mandril 10.

Therefore, the features, characteristics, shapes, construction, and materials of the mandril 160 match the features, characteristics, shapes, construction, and materials of the mandril 10 unless otherwise highlighted here. For example, the mandril 160 includes a shoulder portion, a tapered distal portion, and a distal tip that are the same or similar to the corresponding components of the mandril 10. Additionally, as shown in FIG. 16B, the safety wire 166 may be connected with the mandril 160 during assembly in a similar manner as the safety wire 60 of FIG. 6. For example, the safety wire 166 serves to protect the longitudinal integrity of a coil connected with the safety wire 166.

The mandril 160 of FIG. 16 includes a body portion 162 with a threaded portion 164. In one implementation, the threaded portion 164 comprises external threads raised up from the surface of the body portion 162. The threaded portion 164 serves to hold a connection with the corresponding threaded portion 120 of the cannula 110 of FIGS. 11-13 when the cannula 110 is engaged with the mandril 160.

Figure 17:
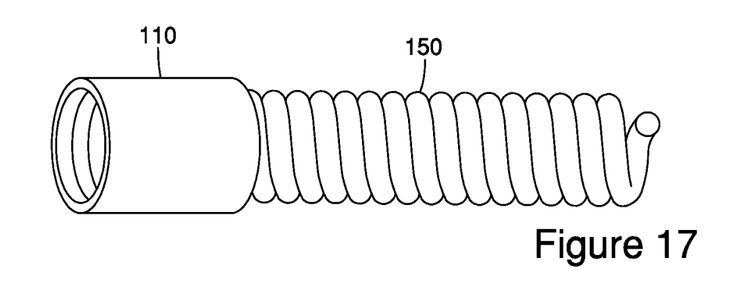
FIGS. 17-19 illustrate a second wire guide assembly using the components of FIGS. 11-16.
Figure 18:
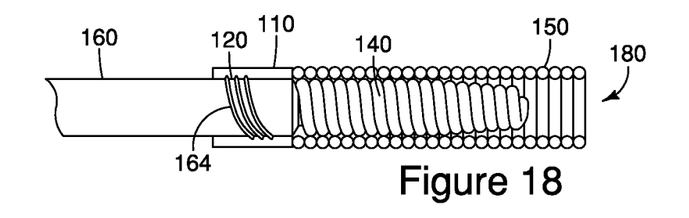
Figure 19:
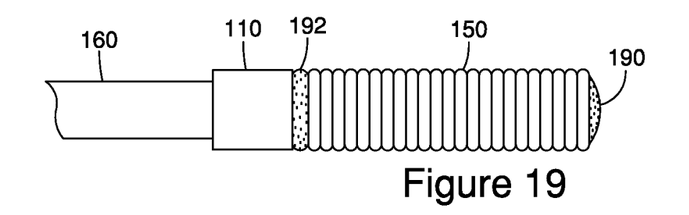

FIGS. 17-19 illustrate a second wire guide assembly using the components of FIGS. 11-16. In FIG. 17, the coil 150 is connected with the cannula 110, such as by soldering the coil 150 to the cannula 110. The coil 150 may be connected with a safety wire to preserve the longitudinal integrity of the coil 150. In FIG. 18, multiple coils are connected with the mandril 160. First, the coil 140 is placed over the safety wire attached to the mandril 160 of FIG. 16. The coil 140 may be connected with the tapered portion of the mandril 160, such as by attaching the coil 140 with solder at the shoulder and tip of the mandril 160. FIG. 18 illustrates that the assembly of the coil 150 and cannula 110 is connected to the mandril 160, which places the coil 140 within an inner cavity 180 of the coil 150. For example, the cannula 110 may be slid over the coil 140 until the threaded portion 120 of the cannula 110 meets the threaded portion 164 of the mandril 160. The cannula 110 is then twisted relative to the mandril 160 to tighten the connection between the mandril 160 and the cannula 110. The cannula 110 and coil 150 can similarly be removed by twisting the cannula 110 relative to the mandril 160 in an opposite direction. FIG. 19 illustrates a completed wire guide using the components of FIGS. 11-16. The distal tip of the coil 150 may include a solder ball 190 or other rounded feature to make the tip of the coil 150 atraumatic. Additionally, the wire guide may include a solder joint 192 to connect the coil 150 with the cannula 110.

Figure 20A:
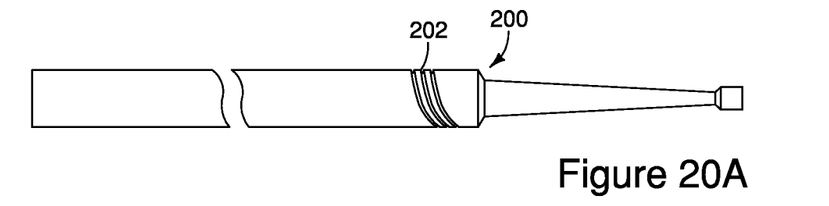
FIGS. 20A, 20B, 21A, and 21B illustrate alternative mandrils for use in the second wire guide assembly of FIGS. 17-19.
Figure 20B:
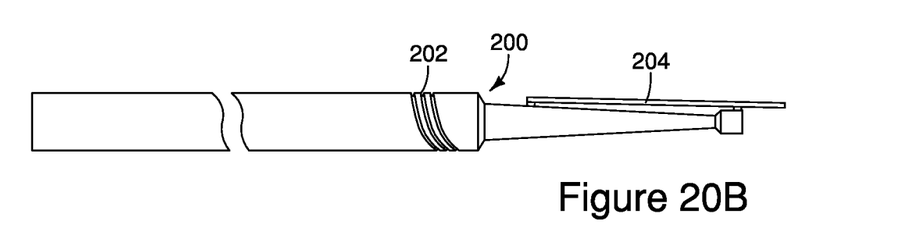

FIG. 20 illustrates an alternative mandril 200 for use in the second wire guide implementation of FIGS. 17-19. FIG. 20A shows the mandril 200 without a safety wire, and FIG. 20B shows a safety wire 204 coupled with the mandril 200. The mandril 200 includes a threaded portion 202 that may be ground into the mandril 200 negatively instead of as a positive profile, such as the positive profile of the threaded portion of the mandril 160 of FIG. 17. For example, the negative profile of the threaded portion 202 may be formed as a channel in the surface of the mandril 160. The negative profile of the threaded portion 202 would connect with positive protruding threads on the inside of a corresponding cannula. The negative profile on the mandril 200 may be beneficial in some implementations because the outer surface of the mandril 200 may not have protruding threads after removal of the cannula and associated outer coil tip.

Figure 21A:
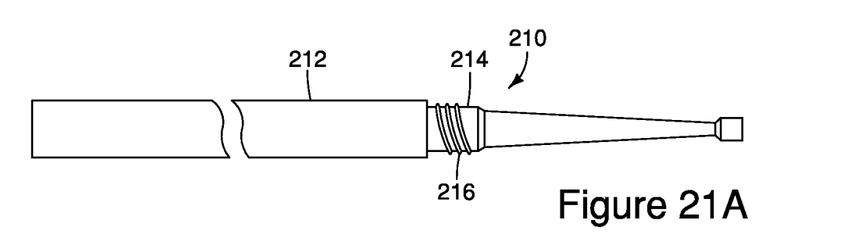
Figure 21B:
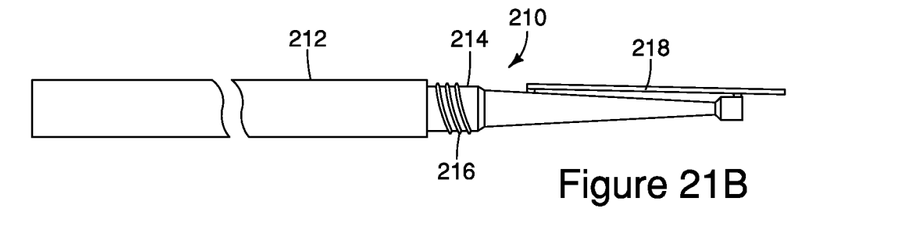
Figure 22:
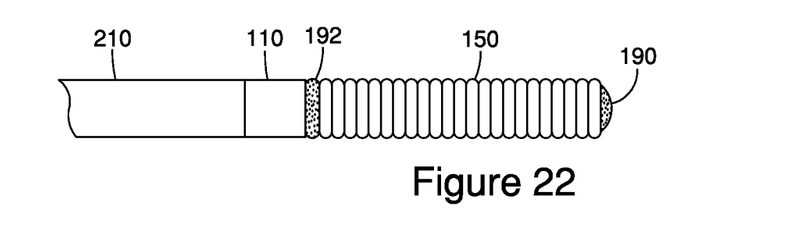
FIG. 22 illustrates a completed wire guide assembly that uses the mandril of FIG. 21.

FIG. 21 illustrates another alternative mandril 210 for use in the second wire guide implementation of FIGS. 17-19. FIG. 21A shows the mandril 210 without a safety wire, and FIG. 21B shows a safety wire 218 coupled with the mandril 210. The mandril 210 includes a body portion with a wider proximal portion 212 and a narrower distal portion 214. The mandril 210 includes a threaded portion 216 on an outer surface of the narrower distal portion 214. FIG. 22 illustrates a completed wire guide assembly that uses the mandril 210 of FIG. 21. Using a mandril with the threaded portion 216 on the narrower distal portion 214 may provide space for the cannula 110 to sit so that the outer surface of the cannula 110 may be substantially flush (e.g., within either a 5%, 10%, or 20% difference in diameter) with an outer surface of the wider proximal portion 212 of the mandril 210 in the completed wire guide assembly, as shown in FIG. 22. Thus, the widest diameter of the completed wire guide assembly of FIG. 22 may be uniform with or without connection of the outer distal tip.

In some implementations, the medical wire guides described herein include two usable tips. Alternative implementations of the wire guide may include more than two usable tips. As one example, one or more additional coils may be interconnected with the outer coil 30 of FIG. 10 in a similar manner as the coil 30 is interconnected with the coil 20. For example, the coil 30 may include a second wider pitch interlocking portion for forming a threaded connection with an additional coil that would provide an inner cavity to contain the coil 30. As another example, one or more additional coils may be interconnected with the wire guide of FIG. 10 by adding a cannula/coil assembly (as shown in FIG. 17) over the coil 30 of the wire guide in FIG. 10.

Figure 23:
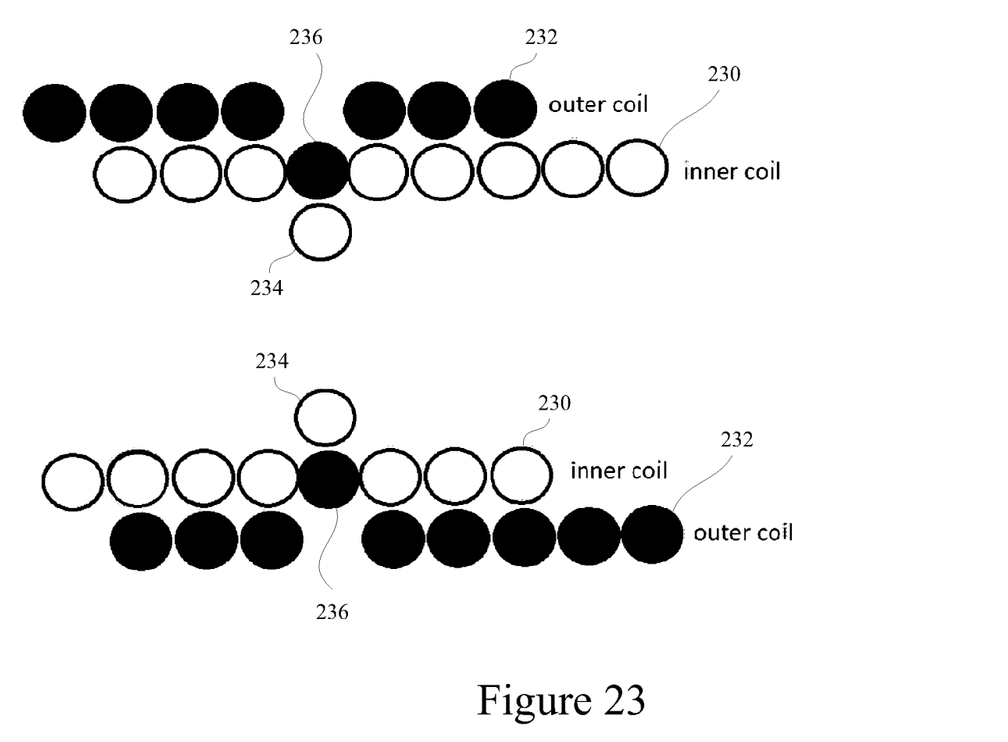
FIG. 23 illustrates an alternative way to connect an inner coil and an outer coil of a wire guide.

The coils of the wire guides described herein may be releasably engaged with each other in several different ways. As one example, FIGS. 8-10 illustrate one way to connect a first coil 20 and a second coil 30. As another example, FIG. 18 illustrates another way to connect a first coil 140 and a second coil 150. Each of these implementations has been described above in more detail. FIG. 23 illustrates still another way to connect an inner coil 230 and an outer coil 232 of a wire guide so that the outer coil 232 defines an inner cavity dimensioned to contain a distal tip of the inner coil 230 when the outer coil 232 is engaged with the inner coil 230. In the implementation of FIG. 23, the inner coil 230 and the outer coil 232 may be pushed towards each other to clip one coil together with the other coil. For example, the coils may be formed with a locking mechanism to clip one coil together with the other coil.

The locking mechanism of the implementation of FIG. 23 may include one or more rings of the coils in a row or separated at intervals. As shown in FIG. 23, a ring 234 of the inner coil 230 may have a smaller dimension (e.g., diameter) than adjacent rings of the inner coil 230. Similarly, a ring 236 of the outer coil 232 may have a smaller dimension (e.g., diameter) than adjacent rights of the outer coil 232. When the ring 236 of the outer coil 232 is aligned with the ring 234 of the inner coil 230, the ring 236 may fit into a void formed from the smaller diameter of the ring 234. In other implementations, multiple rings with a smaller dimension (e.g., diameter) may be positioned adjacent to one another to form a wider interlocking region between the coils. Alternatively, spaced individual rings with a smaller dimension may be positioned in a sequence to provide multiple interlocking regions along the coils.

The connection between the ring 236 and the void formed from the smaller diameter of the ring 234 provides resistance against movement of the outer coil 232 relative to the inner coil 230. However, a physician may intentionally pull the outer coil 232 relative to the inner coil 230 with sufficient force to dislodge the ring 236 from the void formed by the smaller diameter of the ring 234 to remove the outer coil 232 and expose the inner coil 230 for use as the distal tip of the wire guide.

The medical wire guides described herein may be dimensioned to fit within a vascular passage or other body lumen. The wire guide may generally have a length in the range of 30-600 cm. In some implementations, the length of the wire guide may be in the range of 90-300 cm. The wire guide may generally have an outer diameter in the range of 0.204-1.321 mm (0.008-0.052 inches). In some implementations, the outer diameter may be in the range of 0.254-2.286 mm (0.01-0.09 inches). For example, one type of wire guide may have an outer diameter of about 0.889 mm (0.035 inches). In other implementations, wire guides of other dimensions (e.g., longer, shorter, wider, or narrower) may also be used.

While various embodiments, features, and benefits of the present devices have been described, it will be apparent to those of ordinary skill in the art that many more embodiments, features, and benefits are possible within the scope of the disclosure. For example, other alternate devices may include any combinations of structure and functions described above or shown in the figures.

What is claimed is:

1. A medical wire guide, comprising:
   a mandril having a distal tip;
   a first coil coupled with the distal tip of the mandril, the first coil including a first distal end portion having an outer diameter that tapers down towards a first distal tip of the first coil to a smaller outer diameter; and
   a second coil configured to releasably engage with the first coil through an interlocking engagement, where the second coil comprises a second distal tip and defines an inner cavity inside the second coil, the inner cavity defined by an inner diameter of the second coil and dimensioned to contain the first distal end portion of the first coil when the second coil is engaged with the first coil;
   wherein the second coil is coupled with the first coil through a threaded engagement with the first coil that is disconnected by twisting the second coil relative to the first coil.

2. The medical wire guide of claim 1, where the first coil comprises a different material than the second coil.

3. The medical wire guide of claim 1, where the first coil comprises a helical shaped wound coil with a different pitch than the second coil.

4. The medical wire guide of claim 1, where the first coil is wound from a wire with a different diameter than a wire used for the second coil.

5. The medical wire guide of claim 1, where a distal-most portion of the first distal tip of the first coil is soldered to form a first atraumatic distal tip, and where a second distal-most portion of the second distal tip of the second coil is soldered to form a second atraumatic distal tip.

6. The medical wire guide of claim 1, where the first coil is soldered to the mandril.

7. The medical wire guide of claim 1, where the first coil comprises an inner helical shaped wound coil, and where the second coil comprises an outer helical shaped wound coil;
   where the inner coil is wound to have a first interlocking region defined by one or more coil rings with a smaller diameter than an adjacent coil ring on each side of the first interlocking region, and where the outer coil is wound to have a second interlocking region defined by one or more coil rings with a smaller diameter than an adjacent coil ring on each side of the second interlocking region; and
   where the one or more coil rings with the smaller diameter of the outer coil are dimensioned to fit into a void created by the one or more coil rings with the smaller diameter of the inner coil, and where the adjacent coil rings on the sides of the first interlocking region resist at least some movement of the outer coil relative to the inner coil when the second interlocking region is engaged with the first interlocking region.

8. A medical wire guide, comprising:
   a mandril having a distal tip;
   a first coil coupled with the distal tip of the mandril and having a first interlocking portion and a first distal end portion, where the first distal end portion of the first coil tapers down towards a distal tip of the first coil from an outer diameter of the first interlocking portion of the first coil to a smaller outer diameter; and
   a second coil having a second interlocking portion, a second distal end portion, and an inner cavity inside the second coil between the second interlocking portion and the second distal end portion, the inner cavity defined by an inner diameter of the second coil;
   where the first interlocking portion of the first coil is dimensioned to releasably engage with the second interlocking portion of the second coil, and where the first distal end portion of the first coil is contained within the inner cavity of the second coil when the second interlocking portion of the second coil is engaged with the first interlocking portion of the first coil; and
   wherein the first interlocking portion of the first coil defines a space between adjacent rings of the first coil that is dimensioned to fit a corresponding ring of the second coil when the second interlocking portion of the second coil is engaged with the first interlocking portion of the first coil.

9. The medical wire guide of claim 8, where the first coil comprises a helical shaped wound coil with a wider pitch in the first interlocking portion of the first coil than in the first distal end portion of the first coil, and where the second coil comprises a helical shaped wound coil with a wider pitch in the second interlocking portion of the second coil than in the second distal end portion of the second coil.

10. The medical wire guide of claim 9, where the first coil further comprises a proximal end portion, and where the first coil has a wider pitch in the first interlocking portion of the first coil than in the proximal end portion of the first coil.

11. The medical wire guide of claim 8, where the first coil comprises a different material than the second coil.

12. The medical wire guide of claim 8, where the first distal end portion of the first coil comprises a helical shaped wound coil with a different pitch than the second distal end portion of the second coil.

13. The medical wire guide of claim 8, where the first coil is wound from a wire with a different diameter than a wire used for the second coil.

14. The medical wire guide of claim 8, where the first coil is soldered to the mandril, and where the second coil is coupled with the mandril by an indirect connection through a threaded engagement with the first coil that is disconnected by twisting the second coil relative to the first coil.

15. The medical wire guide of claim 8, where a distal-most tip of the first distal end portion of the first coil is soldered to form a first atraumatic distal tip, and where a second distal-most tip of the second distal end portion of the second coil is soldered to form a second atraumatic distal tip.

* * * * *